US00PP20365P3

(12) United States Plant Patent

Abad Álamo et al.

(10) Patent No.: US PP20,365 P3

(45) Date of Patent: Sep. 29, 2009

(54) BLUEBERRY PLANT NAMED 'CARMEN'

(50) Latin Name: *Vaccinium corymbosum*
Varietal Denomination: Carmen

(75) Inventors: Antonio Abad Álamo, Huelva (ES); José Ulf Hayler López, Huelva (ES); Paul M. Lyrene, Micanopy, FL (US)

(73) Assignee: Royal Berries S.L., Huelva (ES)

( * ) Notice: Subject to any disclaimer, the term of this patent is extended or adjusted under 35 U.S.C. 154(b) by 0 days.

(21) Appl. No.: 12/216,695

(22) Filed: Jul. 9, 2008

(65) Prior Publication Data

US 2009/0210974 P1 Aug. 20, 2009

(30) Foreign Application Priority Data

Feb. 14, 2008 (EM) ..... 2008/0339

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para

(74) *Attorney, Agent, or Firm*—Buchanan Ingersoll & Rooney PC

(57) ABSTRACT

A new and distinct Blueberry cultivar is provided that is the product of a controlled breeding program followed by selection. The cultivar flowers early and forms fruit that ripens early. The attractive light blue firm berries exhibit an excellent fruity flavor, are easy to pick, and display a substantial post-harvest shelf life. The plant is self-fertile, and displays a strong generally round to vase-shaped growth habit with foliage that is partially retained during the winter. A low chilling requirement is also exhibited.

8 Drawing Sheets

Botanical/commercial classification: *Vaccinium corymbosum* L./Blueberry Plant.

Varietal denomination: cv. Carmen.

SUMMARY OF THE INVENTION

The new Blueberry cultivar of the present invention was the product of controlled artificial pollination carried out in a greenhouse at Greenwood, Fla., U.S.A., wherein two parents were crossed which previously had been studied in the hope that they would contribute the desired characteristics. The female parent (i.e., the seed parent) was the unreleased 'FL 92-84' cultivar (non-patented in the United States). The male parent (i.e., pollen parent) was the 'FL 95-54' cultivar (non-patented in the United States). The parentage of the new cultivar can be summarized as follows:

'FL 92-84'×'FL 95-54'.

The seeds resulting from the pollination were shipped to Almonte, Huelva, Spain, where they sown during approximately 1997, small plants were obtained which were physically and biologically different from each other and selective research of the progeny was carried out. Selective study resulted in the identification of a single plant of the new cultivar. Initially the plant was designated S01-13-08.

It was found that the new Blueberry plant of the present invention displays the following combination of characteristics:

(a) flowers early and forms fruit that ripens early, (b) displays a strong generally round to vase-shaped growth habit with attractive foliage that is partially retained during the winter, (c) is self-fertile, (d) displays a low chilling requirement, and (e) forms in abundance early in the season attractive light blue firm berries that exhibit an excellent fruity flavor, are easy to pick, and display a substantial post-harvest shelf life.

The new cultivar well meets the needs of the horticultural industry and can be grown to advantage for the commercial production of blueberries.

The new cultivar of the present invention can be distinguished from its ancestors and all other Blueberry cultivars known to its originators. When compared to the 'Sharpblue' cultivar (non-patented in the United States), the new cultivar partially retains its leaves during the winter at Almonte, Huelva, Spain, while the 'Sharpblue' cultivar commonly undergoes complete defoliation. When compared to the 'O'Neal' cultivar (non-patented in the United States), the berries of the are lighter blue in coloration. When compared to the 'Star' cultivar (U.S. Plant Pat. No. 10,675), the growth habit of the new cultivar tends to be more rounded and less upright and commonly assumes a lesser height, and the fruit of the new cultivar commonly matures approximately two weeks earlier than that of the 'Star' cultivar. When compared to the 'Blue Crisp' cultivar (U.S. Plant Pat. No. 11,033) the new cultivar is less susceptible to Rust. When compared to the 'Biloxi' cultivar, the new cultivar is more resistant to Stem Blight.

The new cultivar has been asexually reproduced by the rooting of cuttings beginning during the summer of 2001 at Almonte, Huelva, Spain. Such asexual propagation has shown that the characteristics of the new cultivar are firmly fixed and are stably transmitted from one generation to another. Accordingly, the new cultivar asexually reproduces in a true to type manner.

The new cultivar has been named 'Carmen'.

BRIEF DESCRIPTION OF THE PHOTOGRAPHS

The accompanying photographs show in color as nearly true as it is reasonably possible to make the same in color illustrations of this character, typical plants and plant parts of the new cultivar. The plants which had been asexually reproduced by the rooting of cuttings were approximately five years of age, and were being grown outdoors at Almonte, Huelva, Spain.

FIG. 1 shows during the fruiting season an overall view of a typical fruiting plant of the new cultivar where berries are apparent.

FIG. 2 was obtained on Feb. 1, 2006 and shows the flowers of the new cultivar in various stages of maturity.

FIG. 3 was obtained on Mar. 27, 2006 and shows typical berries of the new cultivar in various stages of maturity as well as typical foliage of the new cultivar.

DETAILED DESCRIPTION

Figure 1:
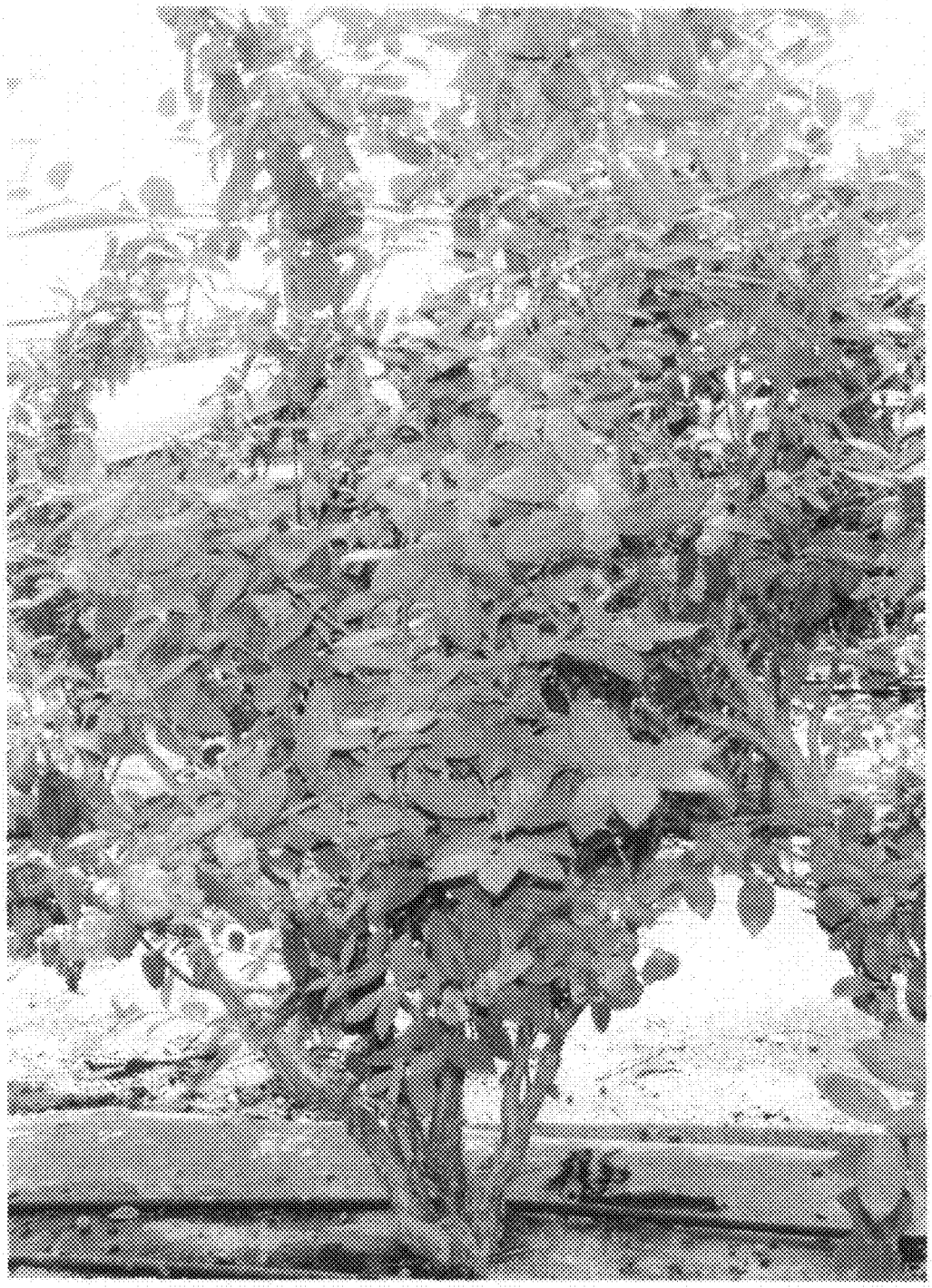
Figure 2:
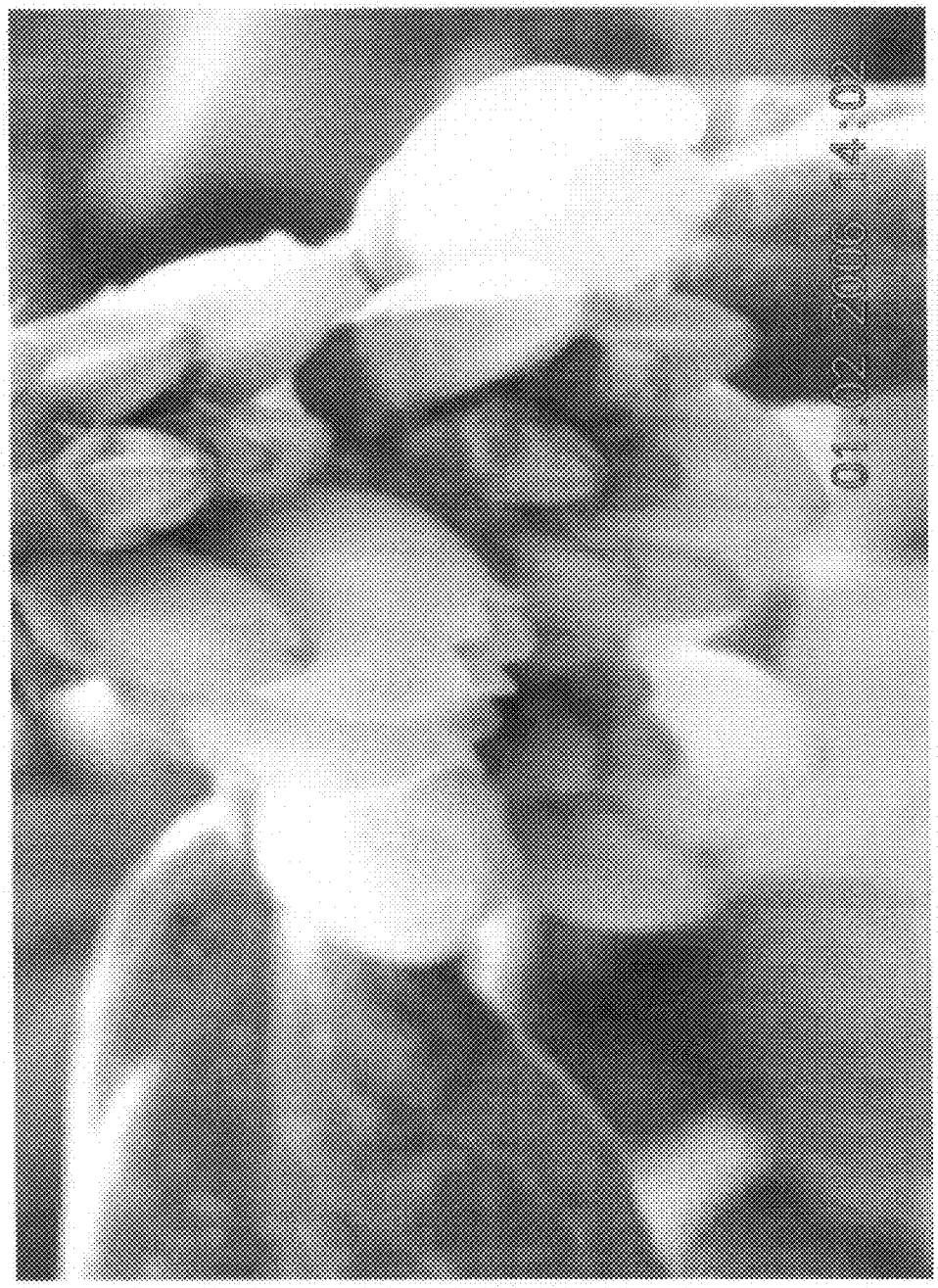
Figure 3:
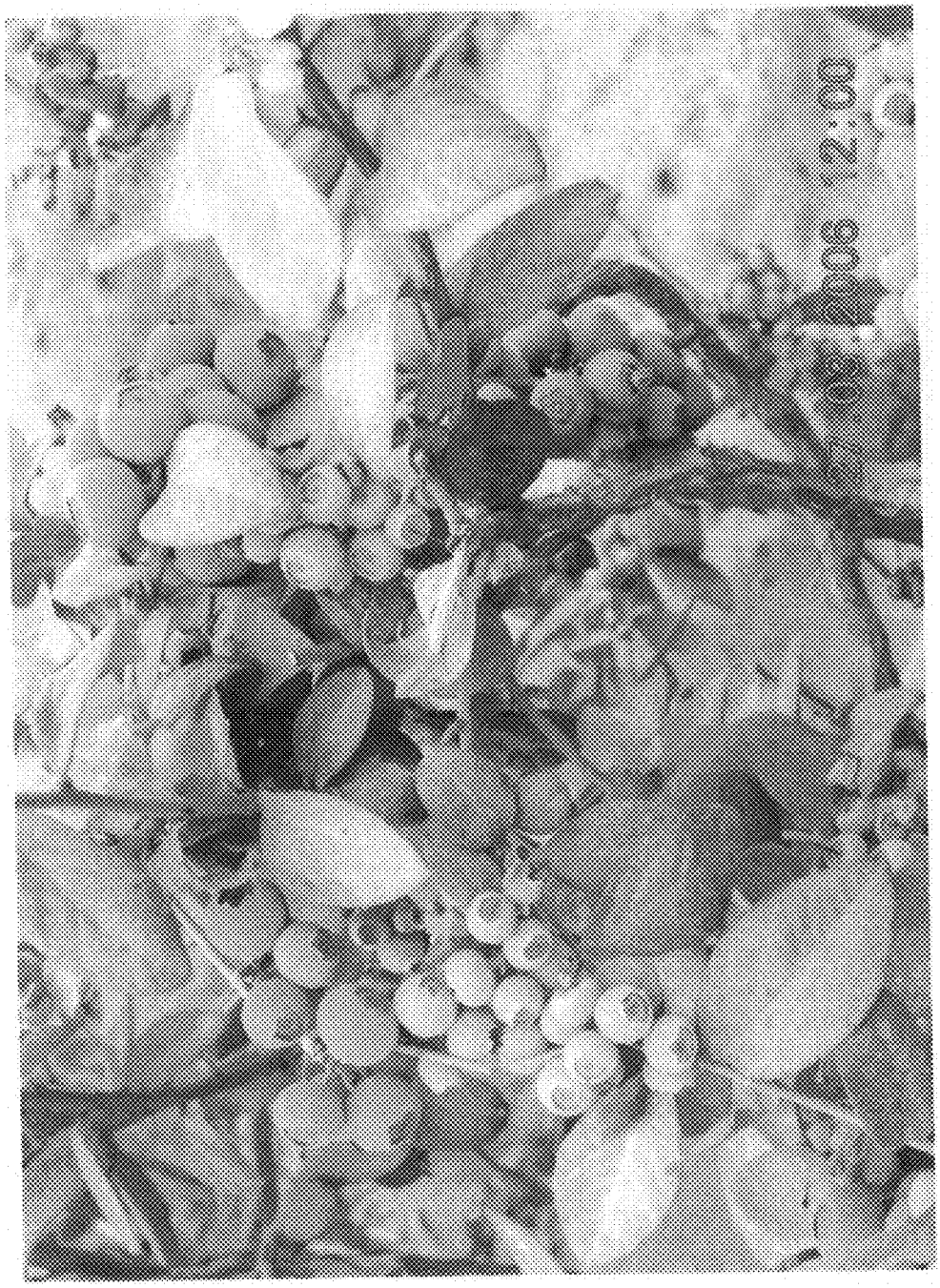
Figure 4:
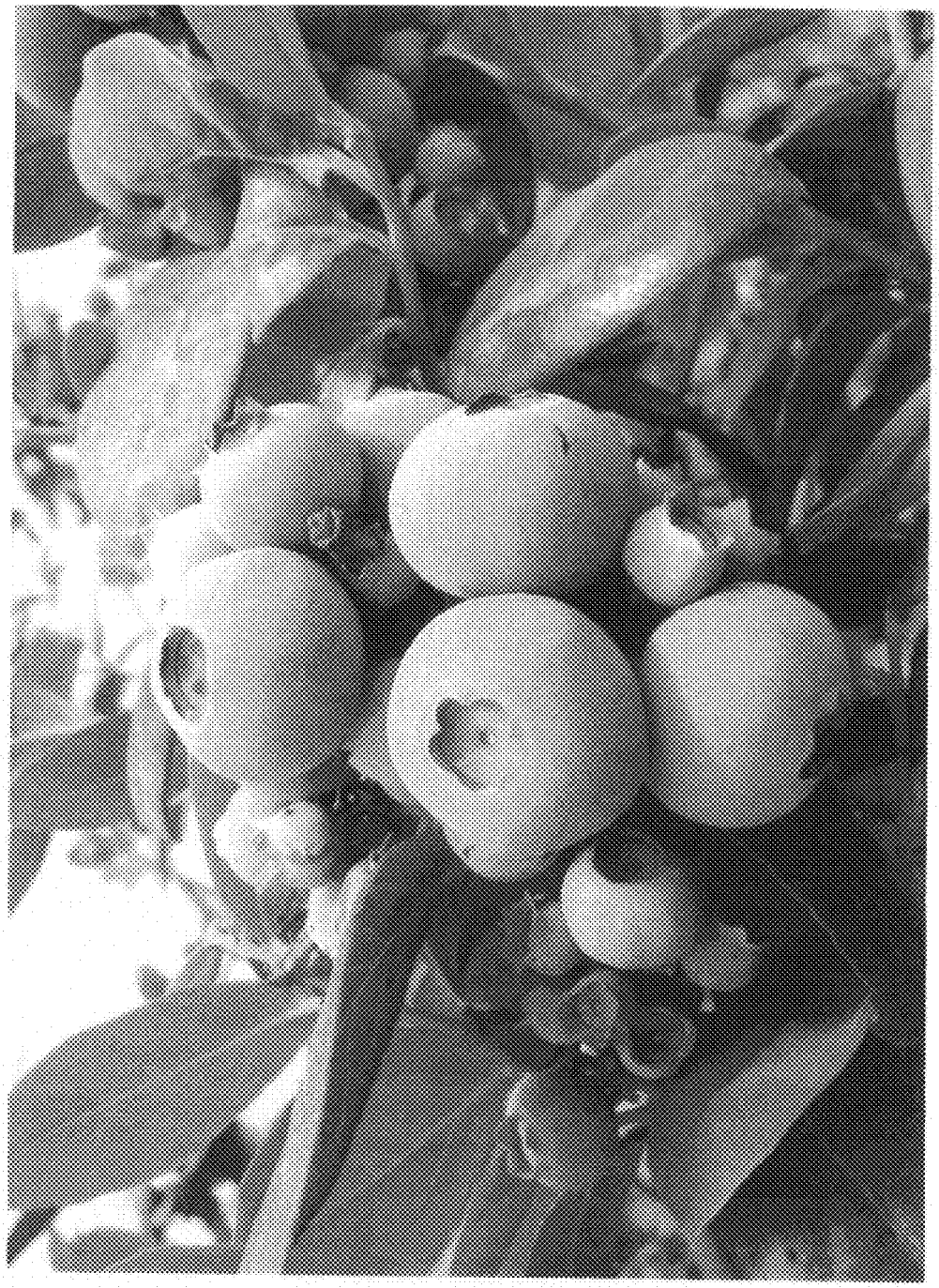
FIG. 4 shows a closer view of typical berries of the new cultivar in various stages of maturity as well as typical foliage of the new cultivar.
Figure 5:
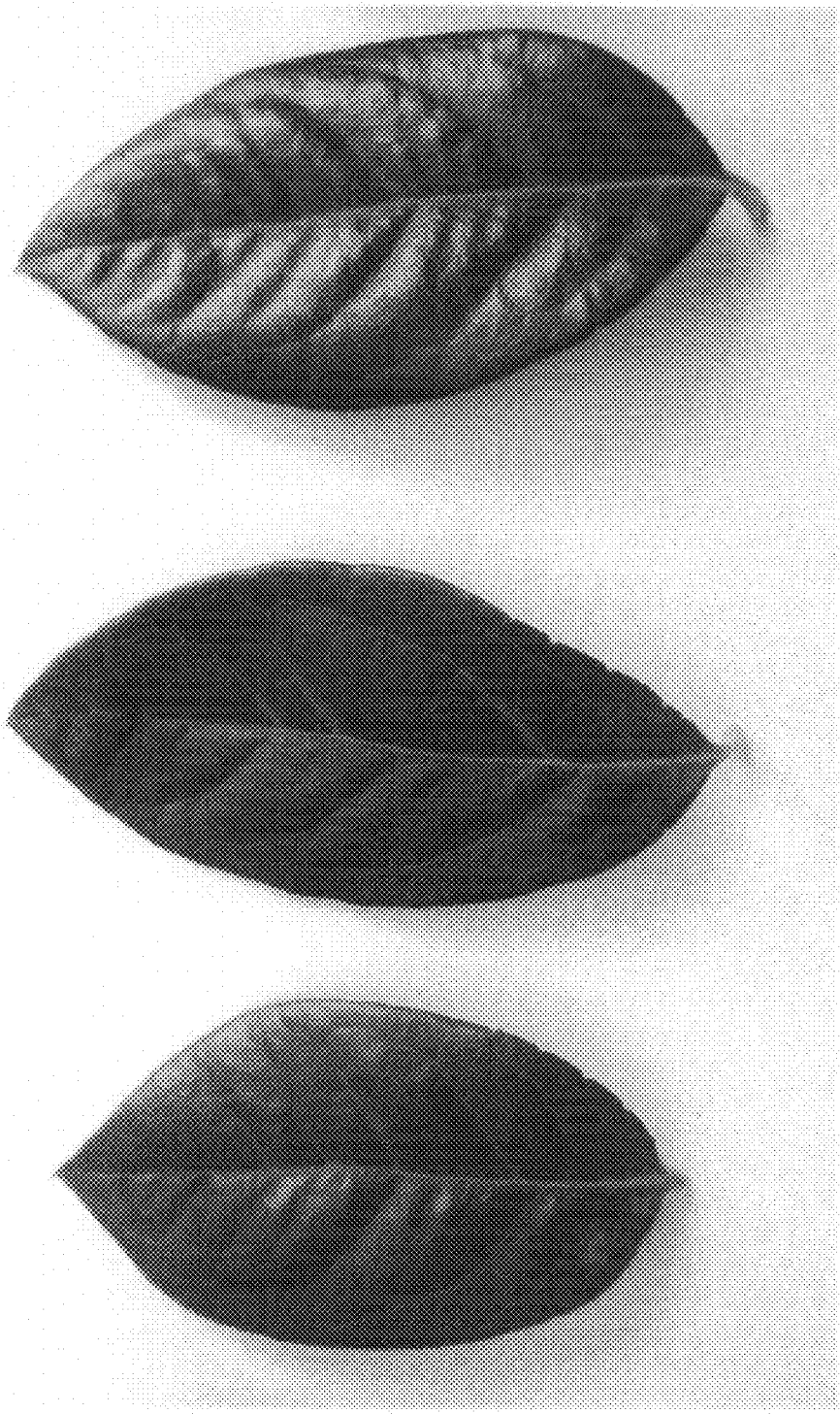
FIG. 5 shows a close view of the upper (adaxial) surfaces of typical leaves of the new cultivar.
Figure 6:
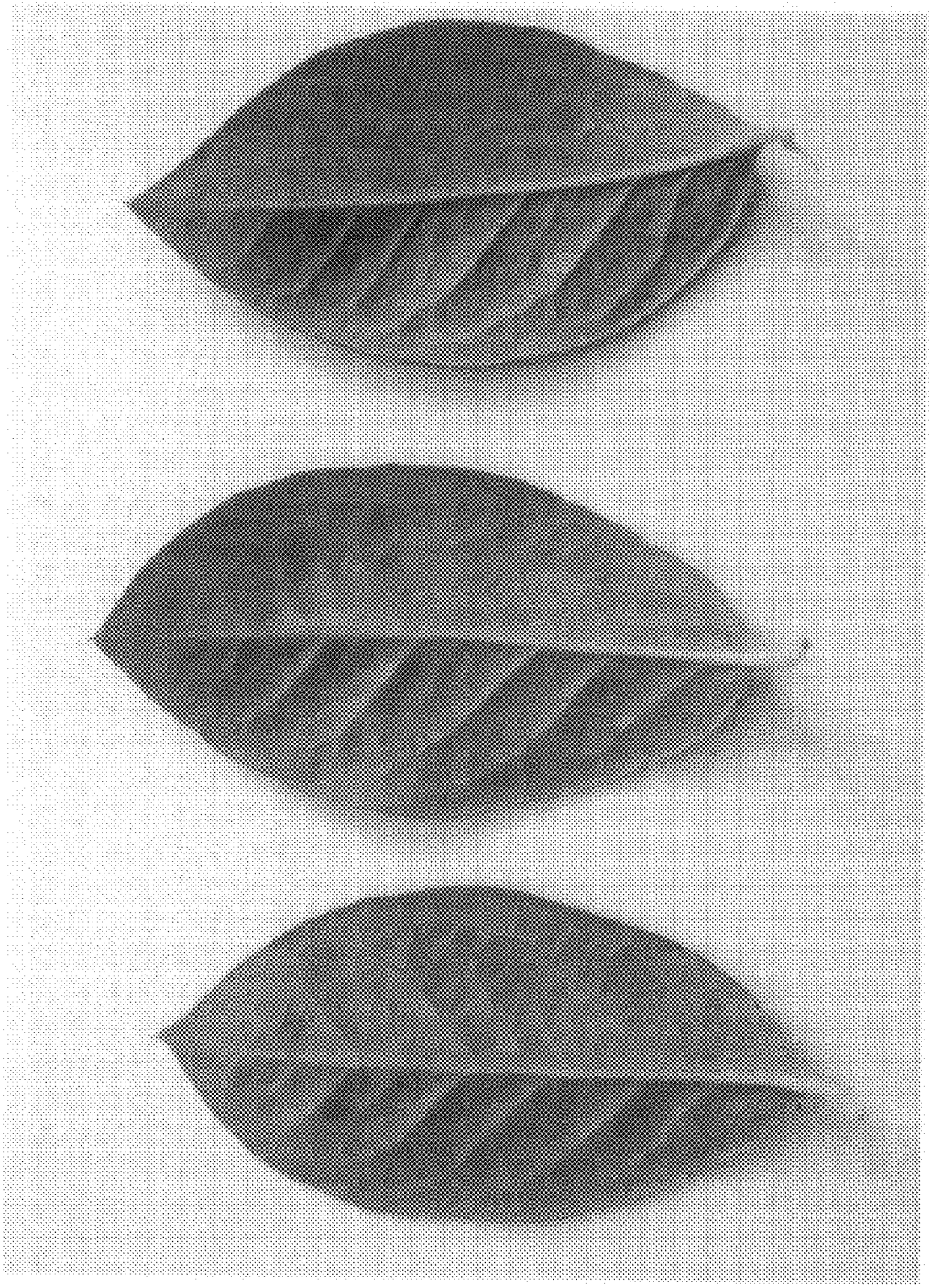
FIG. 6 shows a close view of the under (abaxial) surfaces of typical leaves of the new cultivar.
Figure 7:
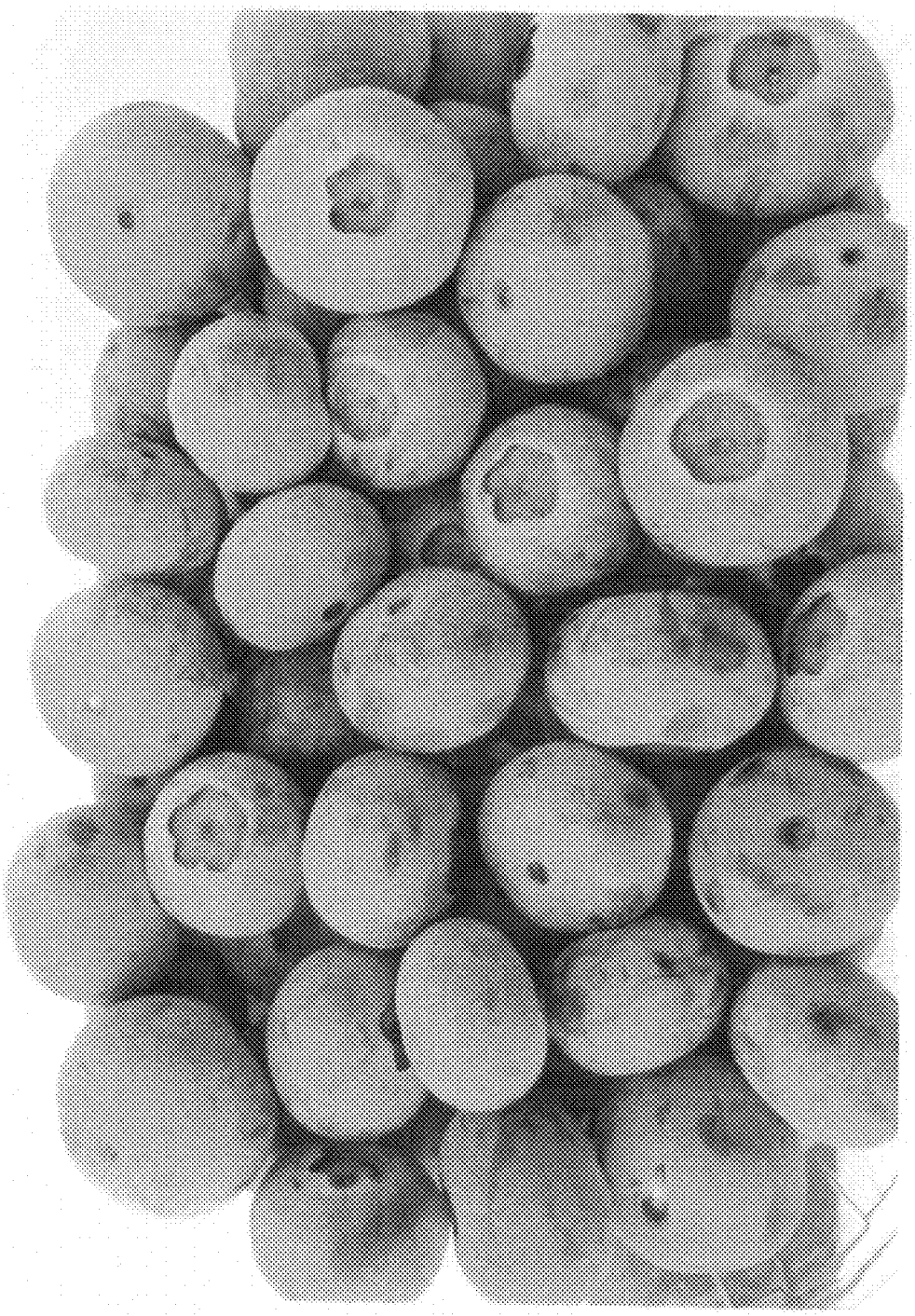
FIG. 7 shows an array of the mature light blue berries of the new cultivar.
Figure 8:
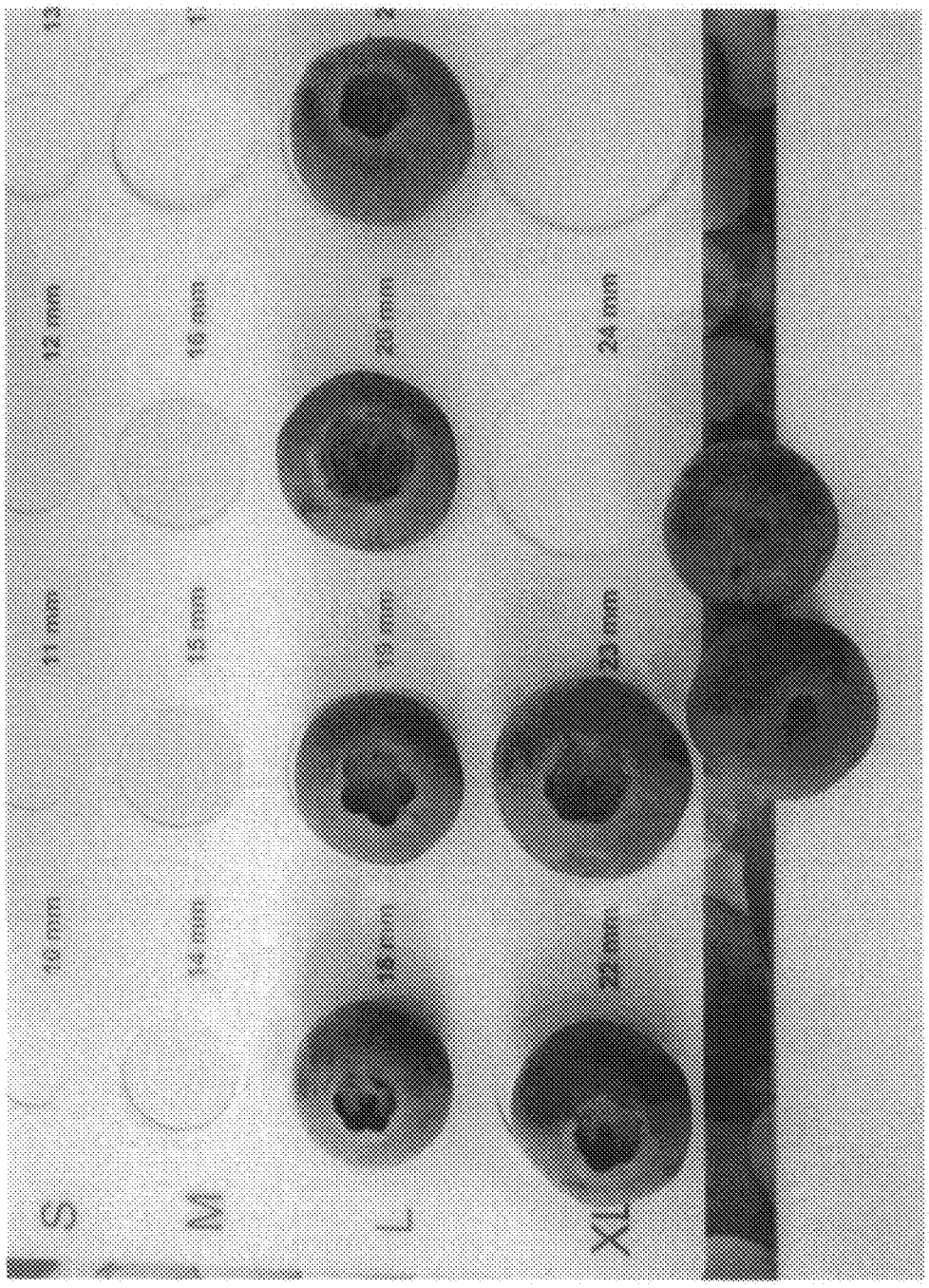
FIG. 8 shows a close view of the mature light blue berries of the new cultivar together with a basis for size comparison.

The chart used in the identification of the colors described herein is The R.H.S. Colour Chart of The Royal Horticultural Society, London, England. Ordinary color terms are to be accorded their customary dictionary significance. The description is based on the observation of approximately five-year-old plants of the new cultivar which had been asexually reproduced by the rooting of cuttings while growing outdoors at Almonte, Huelva, Spain.

Plant:

*Growth habit.*—Generally round to vase-shaped.

*Height.*—Approximately 1.55 m at 5 years of age.

*Width.*—Approximately 3.4 m at 5 years of age.

*Foliage retention.*—Partial retention commonly of approximately 60 percent during the winter at Almonte, Huelva, Spain.

*Chill requirement.*—Less than 300 hours.

Foliage:

*Shape.*—Elliptic.

*Length.*—Commonly approximately 55 mm on average.

*Width.*—Commonly approximately 30 mm on average.

*Apex.*—Acute.

*Base.*—Acute.

*Margin.*—Entire.

*Texture.*—Glabrous and non-glandular.

*Color.*—Green Group 137A on the upper (adaxial) surface, and Green Group 138C on the under (abaxial) surface.

Flowers:

*Time.*—Early at Almonte, Huelva, Spain, with first flower commonly at approximately November 25$^{th}$, and 50 percent bloom at approximately February 25$^{th}$.

*Number.*—Commonly approximately 6 flowers per bud on average.

*Petals.*—5 in number and fused into a corolla tube.

*Fertility.*—Self-fertile.

*Fragrance.*—Light.

Fruit:

*Time.*—Early, commonly from approximately March 7$^{th}$ to May 25$^{th}$ at Almonte, Huelva, Spain (i.e., approximately 10 weeks).

*Shape.*—Generally flattened-round and somewhat pumpkin-shaped (as illustrated).

*Height.*—Commonly approximately 14 mm on average.

*Width.*—Commonly approximately 20 mm on average.

*Weight.*—Approximately 2.63 g/berry on average during 2007 when plants were 4 years of age.

*Fruit scar.*—Approximately 1.35 mm in size on average.

*Fruit scar tear.*—Approximately 5 percent.

*Seed number.*—Commonly approximately 25 per berry on average.

*Seed size.*—Commonly approximately 1.25 mm in length on average and approximately 0.8 mm in width on average.

*Immature color.*—Commonly near Green Group 130D with bloom and Yellow-Green Group 145A without bloom.

*Mature color.*—Light blue, Violet-Blue Group 97A and 97B with bloom and Black Group 202A without bloom.

*Productivity.*—Very abundant, approximately 3.43 Kg/plant on average during 2007 when plants were 4 years of age.

*Flavor.*—Excellent fruity flavor.

Development:

*Ability to store.*—The firm berries are easy to pick, and commonly display a substantial post-harvest shelf life. When stored at 20° C., approximately 78 percent of the harvest commonly is of good quality 7 days after harvest, and when stored at 8° C., approximately 84 percent of the harvest is of good quality 7 days after harvest.

*Disease tolerance.*—No special sensitivity to common Blueberry diseases, such as Leaf Rust (*Pucciniastrum vacinii*) and *Botrytis* Blight (*Botrytis cinerea*) has been encountered during observations to date at Almonte, Huelva, Spain.

*Insects.*—Is susceptible to aphids and thrips.

*Cultural conditions.*—Does well in well drained soils in a low-chilling area.

Plants of the 'Carmen' cultivar have not been observed under all possible environmental conditions to date, Accordingly, it is possible that the phenotypic expression may vary somewhat with changes in light intensity and duration, cultural practices, and other environmental conditions without variance in the genotype.

We claim:

1. A new and distinct Blueberry plant that possess the following combination of characteristics:

(a) flowers early and forms fruit that ripens early, (b) displays a strong generally round to vase-shaped growth habit with attractive foliage that is partially retained during the winter, (c) is self-fertile, (d) displays a low chilling requirement, and (e) forms in abundance early in the season attractive light blue firm berries that exhibit an excellent fruity flavor, are easy to pick, and display a substantial post-harvest shelf life;

substantially as herein shown and described.

* * * * *